United States Patent [19]

Havemann

[11] Patent Number: 4,890,459
[45] Date of Patent: Jan. 2, 1990

[54] MONITOR FOR REFRIGERATION SYSTEM
[75] Inventor: Robert K. Havemann, Bloomington, Minn.
[73] Assignee: Thermo King Corporation, Minneapolis, Minn.
[21] Appl. No.: 281,143
[22] Filed: Dec. 8, 1988
[51] Int. Cl.[4] .............................................. F25B 49/00
[52] U.S. Cl. ........................................ 62/126; 62/129; 62/228.1; 62/158
[58] Field of Search ................ 62/125, 126, 127, 129, 62/158, 195, 85, 475, 228.1; 340/632, 633, 634; 361/22; 73/19, 23, 23.1, 25, 26, 27 R, 27 A

[56] References Cited

U.S. PATENT DOCUMENTS

| | | | |
|---|---|---|---|
| 1,922,666 | 8/1933 | Daynes | 436/138 |
| 3,059,443 | 10/1962 | Garner | 62/126 |
| 3,838,578 | 10/1974 | Sakasegawa et al. | 62/129 X |
| 4,167,858 | 9/1979 | Jojima et al. | 62/126 |
| 4,187,486 | 2/1980 | Takahashi et al. | 338/34 |
| 4,235,095 | 11/1980 | Liebermann | 73/19 |
| 4,316,364 | 2/1982 | Spauschus | 62/129 |
| 4,325,223 | 4/1982 | Cantley | 62/126 |
| 4,344,293 | 8/1982 | Fujiwara et al. | 62/126 |
| 4,637,987 | 1/1987 | Minten et al. | 436/151 |

*Primary Examiner*—Harry B. Tanner
*Attorney, Agent, or Firm*—D. R. Lackey

[57] ABSTRACT

A monitor for detecting air leaks during the operation of a closed vapor compression refrigeration system having a refrigerant compressor driven by a prime mover. An oxygen sensor is disposed in the discharge manifold of the compressor, and the electrical output of the sensor is compared with a reference voltage by a comparator. When an air leak is detected by the comparator, refrigerant control responsive to such detection provides an alarm and/or shuts down the refrigeration system.

5 Claims, 1 Drawing Sheet

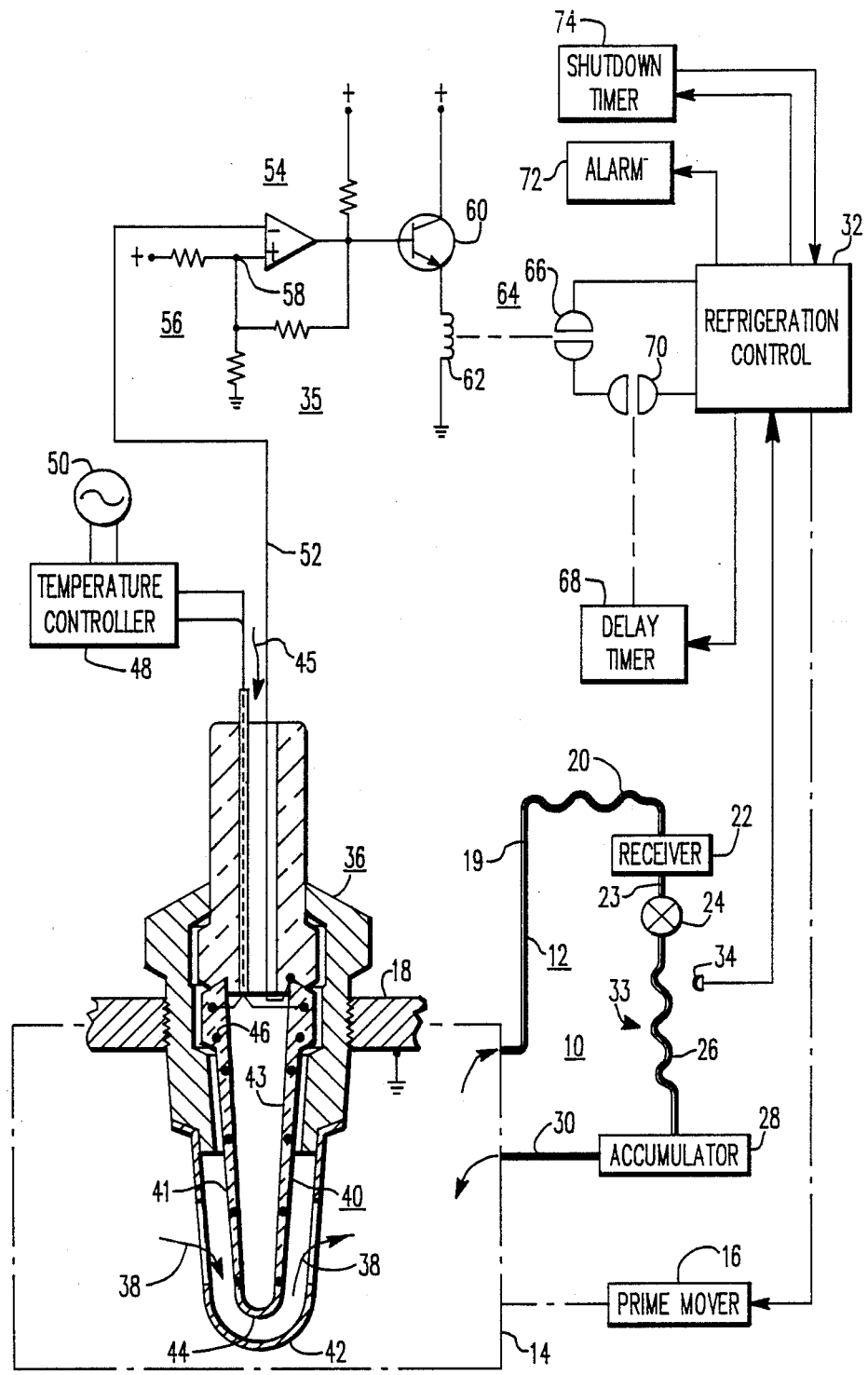

MONITOR FOR REFRIGERATION SYSTEM

TECHNICAL FIELD

The invention relates to refrigeration systems of the vapor compression type, and more specifically to a monitor for detecting improper operation of such refrigeration systems.

BACKGROUND ART

Refrigeration compressors used in refrigeration systems of the vapor compression type are commonly protected against conditions which may cause failure of the compressor, such as by a low oil pressure switch and a high head pressure switch. Air leaks into the closed refrigeration system can cause a catastrophic failure of a compressor, without a detection of a problem in time to save the compressor. Air, being non-condensable, increases head pressure, but the increased pressure may be below the setting of the head pressure sensor and still cause high internal compressor temperatures over a period of time. Over-temperature sensors have not been completely satisfactory in detecting and preventing compressor failure due to air leaks into the refrigeration system.

DISCLOSURE OF THE INVENTION

Briefly, the present invention is a new and improved monitor for refrigeration systems of the vapor compression type, having a refrigerant compressor driven by a prime mover. A zirconia oxygen sensor is disposed in the discharge manifold of the compressor, and its electrical output is monitored by a comparator. A zirconia oxygen sensor provides an electrical output of about 800 millivolts when operated at a suitable stabilizing temperature in a vapor or gas free of oxygen. The electrical output drops in the presence of oxygen, reaching about 200 millivolts when the oxygen partial pressure reaches $10^{-2}$. This voltage drop is detected by the comparator, which provides a suitable signal for the refrigeration control. An alarm for an attendant may be initially given, followed by a shutdown of the refrigeration system if the condition persists for a predetermined period of time.

BRIEF DESCRIPTION OF THE DRAWINGS

The invention will become more apparent by reading the following detailed description in conjunction with the drawing, which is shown by way of example only, wherein the single Figure sets forth a refrigeration monitoring system constructed according to the teachings of the invention.

DESCRIPTION OF PREFERRED EMBODIMENTS

Referring now to the drawing there is shown a refrigeration system 10 to be monitored for air leakage into a closed Freon or refrigerant circuit 12 which includes a refrigerant compressor 14 driven by a prime mover 16, such as an electric motor or an internal combustion engine. Compressor 14 includes a discharge manifold 18 which discharges hot refrigerant vapor into closed refrigerant circuit 12, and a suction manifold (not shown) for receiving refrigerant vapor from circuit 12. Circuit 12 includes a hot gas line 19 which connects discharge manifold 18 to a condenser 20. Condenser 20 rejects heat from the refrigerant and condenses it for temporary storage in a receiver 22. A liquid line 23 connects receiver 22 with an expansion valve 24 which reduces the pressure on the liquid refrigerant and allows the refrigerant to pick up heat and vaporize in an evaporator 26. The vaporized refrigerant is returned to the compressor 14 via an accumulator 28 and a suction line 30. The prime mover 16 is under the control of a refrigeration controller 32, which controller 32 is responsive to the temperature in a space 33 served by evaporator 26 via a temperature sensor 34.

According to the teachings of the invention, refrigeration circuit 12 is monitored for air leaks by a monitor 35 which includes an oxygen sensor 36 disposed in contact with refrigerant 38, indicated by arrows having the same reference numerals. In a preferred embodiment, oxygen sensor 36 is mounted through a tapped opening in the discharge manifold 18 of compressor 14, with the sensor 36 being suitably baffled to prevent oil flooding, or the formation of trapped air bubbles.

Oxygen sensor 36, for example, may be of the type used in the pollution control systems of automobiles in which an electrode 40 formed of a solid zirconium dioxide electrolyte develops a voltage to ground indirectly proportional to the amount of oxygen present across its outer surface 41. The inner surface 43 is vented to the atmosphere, and thus air, indicated by arrow 45, is in contact with surface 43. The inner tip 44 of electrode 40 is mechanically protected by a louvered shield 42, having openings which allow refrigerant vapor 38 to circulate about the outer surface 41 of sensor electrode 40.

In order to provide a voltage which is reliably indicative of oxygen level, the temperature of the zirconium electrode 40 must be maintained in a predetermined temperature range, such as about 250 to 350° C. While automotive exhaust gas will provide the requisite temperature in the hereinbefore mentioned pollution control environment, the temperature of the refrigerant 38 will vary, depending upon type of refrigerant and head pressure. Thus, to insure reliable voltage readings indicative of partial oxygen pressure, sensor 40 is heated to a predetermined temperature. For example a resistance coil 46 may be embedded in electrode 40 and connected to a temperature controller 48, which in turn is connected to a source 50 of electrical potential. A thermistor (not shown), for example, may provide a feedback signal for controller 48 responsive to the temperature of electrode 40.

Electrode 40 will provide a voltage of about 800 millivolts to ground with a 5 megohm load when operating in an absence of oxygen on its external surface 41, while being maintained at a temperature of at least 250° C. If a leak develops in refrigeration circuit 12 which enables air to enter the closed system, the output voltage will drop to about 200 millivolts when the partial oxygen pressure reaches about $10^{-2}$. The amount of air indicated by this amount of oxygen in circuit 12 would cause compressor damage if the compressor 14 is allowed to operate over a period of time, and the present invention detects the voltage change and modifies the operation of the refrigeration system 10 in response to such a detection.

More specifically, an output lead 52 from sensor electrode 40 is connected to a comparator 54, such as comparator type LM29O1. For purposes of example, comparator 54 is shown connected as an inverting comparator with hysteresis, with the inverting input of comparator 54 being connected to the output of sensor 36. The non-inverting input of comparator 54 is connected to a voltage divider 56 and a source of unidirectional potential, to provide a reference voltage at junction 58. The output of comparator 54 is connected to the base of an NPN junction transistor 60 which has its collector connected to a source of unidirectional potential, and its emitter connected to ground via an electromagnetic coil 62 of a relay 64 having a normally open contact 66.

Normally open contact 66 is connected to refrigeration control 32. To insure that time is provided for sensor 36 to reach the desired stable operating temperature, a delay timer 68 having a normally open contact 70 may be provided. Delay timer 68 is actuated by control 32 when refrigeration system 10 is placed in operation. Timer 68 times out and enables monitor 35 by closing and latching its contact 70. In other words, relay contact 66 is connected to control 32 via timer contact 70, and a low initial output voltage level from sensor 36 will not be allowed to send a signal to control 32 which would be interpreted by control 32 as being initiated by an air leak into the closed refrigerant circuit 12. Each time refrigeration system 10 is stopped, delay timer 68 is reset, opening its normally open contact 68.

When refrigerant circuit 12 has no air leak, the 800 millivolt signal applied to comparator 54 will be above the reference level at junction 58 and comparator 54 applies a logic zero to transistor 60, keeping transistor 60 turned off. If air should infiltrate circuit 12, when the oxygen level reaches a value which causes the sensor output voltage to drop below the reference voltage level, the output of comparator 54 will switch to a logic one, turning transistor 60 on and energizing relay 64. Relay contact 66 closes, and if timer 68 has timed out, closing timer contact 68, a signal is applied to refrigeration control 32 which indicates an air leak.

Control 32 may respond to a signal provided by the closed serially connected contacts 66 and 70 by immediately actuating an alarm 72, which may be audio, visual, or both. Control 32 may also initiate the timing of a shut-down timer 74. If the high oxygen signal persists for a predetermined preset period of time, the shutdown timer will time out and provide a shut down signal for control 32. Termination of the air leak signal before timer 74 times out, resets timer 74.

Control 32 responds to the shut down signal provided by timer 74 according to the type of prime mover 16 which is presently driving compressor 14. If an electric motor is driving compressor 14, control 32 may open a contactor which connects the motor to an electrical supply voltage. If an internal combustion engine is driving compressor 14, control 32 may de-energize a fuel solenoid associated with the engine, to stop the engine.

I claim:

1. A monitor for detecting air leaks during the operation of a closed refrigeration system which includes a refrigerant and a compressor having a discharge manifold, comprising:
    an oxygen sensor disposed in contact with refrigerant in the discharge manifold of the compressor,
    said oxygen sensor providing an output voltage indirectly proportional to the amount of oxygen in the refrigerant,
    comparator means for detecting a predetermined change in the voltage provided by said oxygen sensor,
    said comparator means providing a predetermined signal in response to the detection of said predetermined sensor voltage change,
    and control means responsive to the predetermined signal provided by said comparator means.

2. The monitor of claim 1 including means for heating said oxygen sensor to a predetermined temperature.

3. The monitor of claim 1 wherein the control means includes an alarm.

4. The monitor of claim 1 wherein the control means discontinues operation of the compressor.

5. The monitor of claim 2 including delay means for delaying the application of the predetermined signal to the control means until the heating means has heated the oxygen sensor to the predetermined temperature.

* * * * *